（12） United States Patent
Voic et al.

(10) Patent No.: US 9,320,528 B2
(45) Date of Patent: Apr. 26, 2016

(54) ULTRASONIC CUTTING BLADE WITH COOLING LIQUID CONDUCTION

(71) Applicant: Misonix Incorporated, Farmingdale, NY (US)

(72) Inventors: Dan Voic, Cedar Grove, NJ (US); Ronald Manna, Valley Stream, NY (US); Alexander Darian, Brightwaters, NY (US); Scott Isola, Deer Park, NY (US)

(73) Assignee: MISONIX, INCORPORATED, Farmingdale, NY (US)

( * ) Notice: Subject to any disclaimer, the term of this patent is extended or adjusted under 35 U.S.C. 154(b) by 286 days.

(21) Appl. No.: 13/927,619

(22) Filed: Jun. 26, 2013

(65) Prior Publication Data

US 2015/0005774 A1    Jan. 1, 2015

(51) Int. Cl.
| | |
|---|---|
| A61B 17/16 | (2006.01) |
| A61B 17/32 | (2006.01) |
| A61B 17/00 | (2006.01) |
| A61B 18/00 | (2006.01) |
| A61B 17/14 | (2006.01) |

(52) U.S. Cl.
CPC ............ *A61B 17/1644* (2013.01); *A61B 17/16* (2013.01); *A61B 17/320068* (2013.01); *A61B 17/141* (2013.01); *A61B 2017/00831* (2013.01); *A61B 2017/1651* (2013.01); *A61B 2018/00029* (2013.01); *A61B 2018/00065* (2013.01); *A61B 2217/007* (2013.01)

(58) Field of Classification Search
CPC ........... A61B 17/320068; A61B 2017/320084; A61B 17/1644
See application file for complete search history.

(56) References Cited

U.S. PATENT DOCUMENTS

| | | | | |
|---|---|---|---|---|
| 3,786,814 | A * | 1/1974 | Armao | 606/23 |
| 4,169,984 | A * | 10/1979 | Parisi | 310/323.18 |
| 4,832,683 | A * | 5/1989 | Idemoto et al. | 604/22 |
| 4,974,581 | A * | 12/1990 | Wiksell | 601/2 |
| 5,139,504 | A * | 8/1992 | Zelman | 606/127 |
| 5,167,725 | A * | 12/1992 | Clark et al. | 428/680 |
| 5,188,102 | A * | 2/1993 | Idemoto et al. | 604/22 |
| 5,205,817 | A * | 4/1993 | Idemoto et al. | 604/22 |
| 5,221,282 | A * | 6/1993 | Wuchinich | 606/99 |
| 5,261,922 | A * | 11/1993 | Hood | 606/167 |
| 5,324,299 | A * | 6/1994 | Davison et al. | 606/167 |
| 5,358,505 | A * | 10/1994 | Wuchinich | 606/99 |
| 5,382,251 | A * | 1/1995 | Hood et al. | 606/99 |
| 5,674,235 | A * | 10/1997 | Parisi | 606/169 |
| 6,267,594 | B1 * | 7/2001 | Hugo | 433/119 |
| 6,283,981 | B1 * | 9/2001 | Beaupre | 606/169 |
| 6,379,371 | B1 * | 4/2002 | Novak et al. | 606/169 |
| 6,443,969 | B1 * | 9/2002 | Novak et al. | 606/169 |
| 8,016,843 | B2 * | 9/2011 | Escaf | 606/166 |
| 8,343,178 | B2 * | 1/2013 | Novak et al. | 606/169 |

(Continued)

*Primary Examiner* — Christian Sevilla
(74) *Attorney, Agent, or Firm* — R. Neil Sudol; Henry D. Coleman

(57) ABSTRACT

An ultrasonic surgical tool has probe body with an operative surface or edge contactable with organic tissues for performing a surgical operation on the tissues. A shank of the probe body is provided with a connector for operatively attaching the tool to a source of ultrasonic mechanical vibrational energy. The shank and a portion of the probe body are formed with a channel for fluid delivery to the probe body. At least a portion of the probe body located between the channel and the operative surface or edge has a microporous or sintered structure enabling fluid penetration to the operative surface or edge from the channel.

9 Claims, 1 Drawing Sheet

(56) References Cited

U.S. PATENT DOCUMENTS

| | | | |
|---|---|---|---|
| D680,218 S * | 4/2013 | Darian et al. | D24/144 |
| 2002/0077550 A1* | 6/2002 | Rabiner et al. | 600/439 |
| 2002/0077643 A1* | 6/2002 | Rabiner et al. | 606/169 |
| 2002/0091404 A1* | 7/2002 | Beaupre | 606/169 |
| 2002/0103497 A1* | 8/2002 | Satou | 606/169 |
| 2003/0036705 A1* | 2/2003 | Hare et al. | 600/437 |
| 2003/0069590 A1* | 4/2003 | Rabiner et al. | 606/128 |
| 2004/0030254 A1* | 2/2004 | Babaev | 600/459 |
| 2005/0177184 A1* | 8/2005 | Easley | 606/167 |
| 2005/0273127 A1* | 12/2005 | Novak et al. | 606/169 |
| 2006/0241470 A1* | 10/2006 | Novak et al. | 600/459 |
| 2007/0233131 A1* | 10/2007 | Song et al. | 606/79 |
| 2008/0009848 A1* | 1/2008 | Paraschiv et al. | 606/34 |
| 2008/0058775 A1* | 3/2008 | Darian et al. | 606/1 |
| 2008/0194999 A1* | 8/2008 | Yamaha et al. | 601/2 |
| 2008/0234710 A1* | 9/2008 | Neurohr et al. | 606/169 |
| 2008/0300591 A1* | 12/2008 | Darian et al. | 606/41 |
| 2011/0105958 A1* | 5/2011 | Babaev | 601/2 |
| 2011/0196287 A1* | 8/2011 | Robertson et al. | 604/22 |
| 2011/0196398 A1* | 8/2011 | Robertson et al. | 606/169 |
| 2011/0196400 A1* | 8/2011 | Robertson et al. | 606/169 |
| 2013/0204285 A1* | 8/2013 | Gouery et al. | 606/169 |
| 2015/0005774 A1* | 1/2015 | Voic et al. | 606/82 |
| 2015/0057692 A1* | 2/2015 | Voic | 606/169 |
| 2015/0088137 A1* | 3/2015 | Manna | 606/79 |

* cited by examiner

ULTRASONIC CUTTING BLADE WITH COOLING LIQUID CONDUCTION

FIELD OF THE INVENTION

This invention relates to an ultrasonic tool. More particularly, this invention relates to an ultrasonic cutting blade. The blade is particularly useful in a surgical application to cut tissue such as cartilage and bone. The present invention is also directed in part to an associated surgical method.

BACKGROUND OF THE INVENTION

In the field of orthopedics, the cutting of living bone is a prerequisite for many procedures. Such procedures include the reconstruction of damaged tissue structures due to accidents, the grafting of healthy bone into areas damaged by disease, or the correction of congenital facial abnormalities like a receding chin line. Over several centuries, these tasks were performed through the utilization of devices called bone saws.

Traditional bone saws are categorized into several basic categories. Hand powered saws or drills are just that, hand held devices which require the operator to move the device in a fashion similar to that used for carpentry tools. Powered devices, whether electric or pneumatic, are of either the reciprocating or rotary type. The reciprocating devices use a flat, sword like blade where the back and forth motion is provided by a motor instead of the hand. The rotary devices use a rotating motor to spin a drill bit or a blade that has teeth arranged around its circumference similar to a table saw blade. All of these traditional bone saws are used today in medical procedures around the world.

While traditional saws are functional, they have many disadvantages. With either the band or reciprocating saws, for instance, it is not easy to initiate and direct a cut. A cut must start from an edge or, alternatively, a starting hole must be used. To create a starting hole, a drill or similar instrument is operated to bore into the bone. Subsequently, a cutting blade is inserted into the bored hole. The user can then proceed to cut. Alternatively, a rotary type blade may be used. However, when a rotary blade is used, the cut must follow a relatively straight path to prevent the blade from binding in the cut. With all blades the ability to create a curved or compound angle cut is extremely limited by the blade chosen. The relatively thick blades have a wide kerf, so that a significant thickness of the viable bone is lost in the cutting procedure. Physicians would like this width to be as thin as possible in most procedures where reconstruction is necessary.

Above all, the relatively slow linear or tangential speeds of conventional bone saw blades coupled with the teeth necessary for cutting result in high frictional losses, which becomes manifested as heat. Heat will cause necrosis of the tissue if the bone temperatures reach 47° C. for more than a few seconds. When tissue necroses, the bone recedes after the surgery as the necrotic bone is overgrown. During such natural post-surgical tissue developments, the thickness of the cuts in the bone actually increases. The bone rescission process must be complete before healing can begin. To prevent the shortening of the length of the bone, metal plates and screws are used to fix the bone fragments in proper position. All of these factors obviously lead to increased operative time, and more importantly, to dramatically increased healing time, since the bone must knit across a greater span. Some studies have shown the strength of the bone to be effected negatively as well When an upper or lower jaw is to be cut in elective surgery, the heating effect of traditional saws requires even more extraordinary intervention to prevent damage. Cutting the jaw between the teeth will cause loss of teeth if the bone is damaged or does not heal quickly. To prevent the tooth loss, the teeth must be spread apart preoperatively; sometimes forcing the patient to wear braces for up to 6 months before the operation can take place. In these cases, the costs and patient discomfort increases dramatically.

To limit the tissue temperature rise in an attempt to reduce necrosis, some traditional surgical saws provide cooling liquid to the surgical site. See, for instance, U.S. Pat. No. 4,008,720 to Brinckmann et al. These devices typically introduce coolant into spaces between segments on the cutting edge or rely on spray methods to flood the cutting site with fluid. Another technique employed by clinicians is to make very light cuts and increase the time between passes of the tool. Coupled with irrigation of the area, bone temperature rise is reduced measurably. Of course, this technique increases operative time and clinician fatigue.

Several researchers have proposed the use of ultrasonic tools for bone separation. The use of ultrasonic surgical instruments for cutting through various tissues is well known. While these devices are superior to the traditional saws in several aspects such as reduced kerf size, reduced noise, and superior ability for making complex geometric cuts, the temperature rise in bone due to frictional heating at the blade/tissue interface is still a significant problem. The problem is exacerbated with the use of ultrasonics due to the rapid motion involved as compared to that of traditional reciprocating saws. Some designers have tried to reduce heating by modifying the cross-section of the cutting blade. U.S. Pat. No. 5,188,102 to Idernoto, U.S. Pat. No. 4,188,952 to Loschilov, and U.S. Pat. No. 5,261,922 to Hood all show designs for cutting which have modified cross sections to reduce frictional heating.

Several ultrasonic devices have provided cooling to the cutting blade with varied degrees of success. U.S. Pat. No. 4,823,790 to Alperovich et al. shows a design for a cryogenically cooled scalpel blade. However, this design may actually damage viable tissue by freezing. In addition, this design does not provide any coolant to surrounding tissue not in direct contact with the blade.

U.S. Pat. Nos. 5,205,817, 5,188,102, and 4,832,683 all to Idemoto show examples of ultrasonic instruments with provisions for fluid cooling. These instruments, however, either do not provide optimal coolant flow where it is needed, mainly at the cutting portion of the blade, or for ones that do provide coolant at the tip, they interrupt the cutting edge with holes for the coolant. An interrupted, uneven cutting edge hinders manipulation and makes it difficult to guide the blade on the bone surface.

One phenomenon associated with ultrasonic tooling which acts to hinder the beneficial effects of irrigating the operative site is ultrasonic atomization. When an ultrasonically vibrating body is brought into contact with fluid, that fluid is broken into small droplets, which have a size inversely proportional to the frequency of vibration. In other words, the higher the frequency, the smaller and more mobile the liquid drop. Droplets created by ultrasonic vibrations can be very small in size, with some being less than 1 micron in diameter. This phenomenon is well known to the art. In fact, many devices intended to atomize liquid, such as room humidifiers, medical nebulizers, and industrial spray nozzle are based upon this principle. In the operating theater, however, the presence of nebulized particles is not appreciated, since these particles may contain viral or bacterial agents. Also, some of the fluid will be atomized before reaching the operative site, reducing the cooling efficiency. An effective way to insure the liquid transport is needed.

U.S. Pat. No. 6,379,371 discloses an ultrasonic surgical blade with cooling, which has a blade body with a smooth continuous cutting edge and a shank connected at one end to the blade body and operatively connectable at an opposite end to a source of ultrasonic vibrations. The shank is provided with an axially extending bore for the conveyance of cooling fluid to the cutting edge, while the blade body is provided with an axially extending through-slot communicating at one end with the bore. The blade body is preferably provided at an end opposite the shank with a recess communicating, with the bore for distributing fluid from the slot towards the cutting edge. The recess may have a configuration that parallels at least a portion of the cutting edge. Where the cutting edge is circular and the blade body has a planar surface between the fluid distribution guide surface and the cutting edge, for instance, the recess has a fluid distribution surface inclined with respect to the planar blade surface and extending along a circular arc.

SUMMARY OF THE INVENTION

The present invention aims to provide an improved ultrasonic tool or probe which has an improved cooling capability. An ultrasonic tool or probe in accordance with the invention may particularly take the form of ultrasonic cutting blade which allows thin kerf cuts, does not require predrilled holes for cutting, allows complex geometric cuts, has a continuous cutting surface, and provides for liquid irrigation at primarily the blade/tissue interface. More specifically, the present invention pertains to an ultrasonically vibrated cutting blade with an improved provision for delivery of a cooling medium for reducing and limiting thermal damage to living tissue. The present invention specifically targets the application of cutting viable bones in surgery, although the device is not exclusive to this application.

An ultrasonic surgical tool in accordance with the present invention comprises a probe body that has an operative surface or edge contactable with organic tissues for performing a surgical operation on the tissues. The tool further comprising a shank connected to a proximal end of the probe body and provided at an end opposite the blade body with a connector for operatively attaching the tool to a source of ultrasonic mechanical vibrational energy. The shank and a portion of the probe body are formed with a channel for fluid delivery to the probe body. At least a portion of the probe body located between the channel and the operative surface or edge has a microporous structure enabling fluid penetration to the operative surface or edge from the channel.

The channel may include a main section extending longitudinally along the probe body and at least one branch section extending at least partially transversely from the main section toward the operative surface or edge. The branch section of the channel extends only partway from the main section toward the operative surface or edge has a free end opposite the main section and spaced from the operative surface or edge.

Preferably, at least the portion of the probe body between the channel and the operative surface or edge is made of sintered material. The probe body may be made in its entirety of the sintered material.

The liquid infeed channel may include a plurality of branch sections each extending at least partially transversely from the main section of the channel toward the operative surface or edge of the probe body, each of the branch sections extending only partway from the main section toward the operative surface or edge, each of the branch sections having a respective free end opposite the main section and spaced from the operative surface or edge. The portions of the probe body between the ends of the various branch sections and an outer surface or edge of the probe body are preferably made of sintered material.

The probe body may take the form of a flattened or planar cutting blade having a pair of opposed major surfaces defined by a pair of opposed longitudinal edges and a distal edge of the blade, the operative surface or edge extending in part along one of the longitudinal edges and in part along the distal edge. The blade is made partially or wholly of sintered material to enable liquid conduction from the infeed channel to the outer surfaces and/or edges of the blade.

The microporous structure in an ultrasonic tool or probe in accordance with the present invention defines or enables a multiplicity of micropore pathways extending from the liquid infeed channel to the operative surface or edge, the probe body being devoid of other pathways for liquid flow from the channel to the operative surface or edge.

A surgical method in accordance with the present invention comprises providing an ultrasonic surgical tool having a probe body and a shank connected at a proximal end thereof, the probe body having an operative surface or edge, the shank and the probe body being formed with a channel, at least a portion of the probe body extending between the channel and the operative surface or edge having a microporous structure. The method further comprises operatively connecting a proximal end of the shank to a source of ultrasonic mechanical vibrations, operatively coupling the channel to a source of liquid, moving the probe body to a surgical site on a patient, and placing the operative surface or edge in contact with organic tissues at the surgical site. While the operative surface or edge is in contact with the organic tissues, ultrasonic mechanical vibrations are generated in the probe body, thereby ultrasonically vibrating the operative surface or edge. While the operative surface or edge is in contact with the organic tissues and during the generating of the ultrasonic mechanical vibrations in the probe body, one feeds liquid under pressure from the source of liquid into the channel and from the channel through multiple micropore pathways in the probe body to the operative surface or edge.

As indicated above, the probe body is devoid of other pathways for liquid flow from the channel to the operative surface or edge. Accordingly, a feeding of liquid under pressure from the source of liquid to the operative surface or edge of the probe body includes moving liquid along only the micropore pathways between the channel and the operative surface or edge.

The probe body may take the form of a flattened or planar cutting blade having a pair of opposed major surfaces defined by a pair of opposed longitudinal edges and a distal edge, the operative surface or edge extending in part along one of the longitudinal edges and in part along the distal edge. The method then further comprises cutting into the organic tissues by virtue of the generating of ultrasonic mechanical vibrations in the probe body and the ultrasonic vibrating of the operative surface or edge.

DETAILED DESCRIPTION

Figure 1:
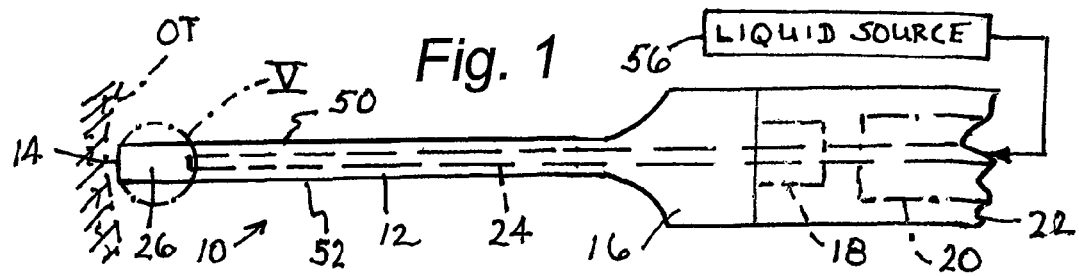
FIG. 1 is a schematic side elevational view of an ultrasonic surgical tool, blade or probe in accordance with the present invention.
Figure 2:
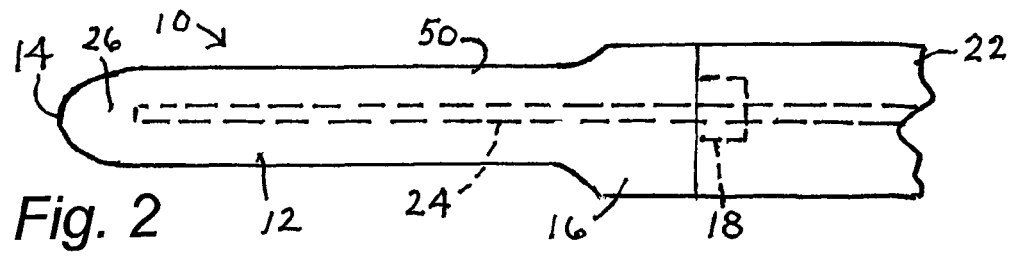
FIG. 2 is a top plan view of the ultrasonic surgical tool, blade or probe of FIG. 1, showing one configuration of a liquid-delivery channel in the tool, blade or probe.

As depicted in FIGS. 1 and 2, an ultrasonic surgical tool 10 comprises a probe body 12 that has an operative surface or edge 14 contactable with organic tissues OT for performing a surgical operation on the tissues. Tool 10 further comprises a shank 16 connected to a proximal end of probe body 12 and provided at an end opposite the probe body with a connector 18 for operatively attaching the tool to a source 20 of ultrasonic mechanical vibrational energy, for instance, a piezoelectric or magnetoconstrictive transducer in a handpiece 22. Shank 16 and a portion of the probe body 12 are formed with a channel 24 for fluid delivery to the probe body. At least a portion 26 of the probe body located between channel 24 and operative surface or edge 14 has a microporous structure 28 (FIG. 5) enabling fluid penetration to the operative surface or edge from the channel.

Figure 3:
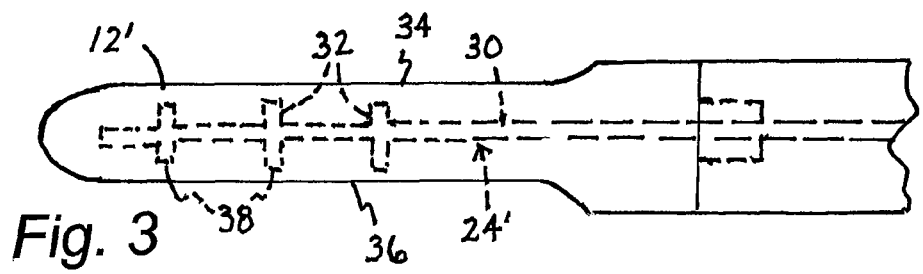
FIG. 3 is a top plan view similar to FIG. 2, showing another configuration of a liquid-delivery channel in the tool, blade or probe.

In the embodiment of FIGS. 1 and 2, channel 24 takes the form of a linear bore extending centrally through shank 16 and probe body 12. However, as shown in FIG. 3, a channel 24' in a blade or probe body 12' alternatively includes a main longitudinal section 30 extending longitudinally along probe body 12 and one or more auxiliary or branch sections 32 extending transversely or perpendicularly from main section 30 towards operative surfaces or edges 34 and 36 which are oriented longitudinally along probe body 12'. Branch sections 32 of channel 24' extend only partway from main section 30 toward operative surfaces or edges 34 and 36 and have respective free ends 38 opposite main section 30 and spaced from the operative surfaces or edges 34, 36. In FIG. 3, blade or probe body 12' has a microporous structure (28 in FIG. 5), preferably throughout but at least in the areas between the ends 38 of branch sections 32 and blade edges 34 and 36, enabling fluid penetration to the operative surface or edge from the channel 24'.

Figure 4:
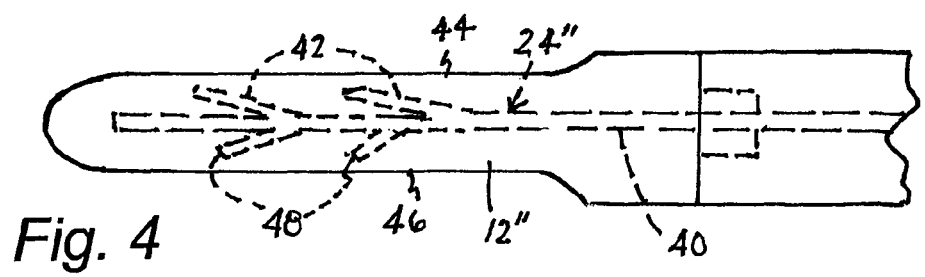
FIG. 4 is a top plan view similar to FIGS. 2 and 3, showing a further configuration of a liquid-delivery channel in the tool, blade or probe.

FIG. 4 illustrates another version of channel 24. As shown in FIG. 4, a channel 24" alternatively includes a main longitudinal section 40 extending longitudinally along a blade or probe body 12" and one or more inclined or angled branch sections 42 extending partially transversely and partially longitudinally from main section 40 towards longitudinal operative surfaces or edges 44 and 46 of probe body 12". Branch sections 42 of channel 24" extend only partway from main section 40 toward operative surfaces or edges 44 and 46 and have respective free ends 48 opposite main section 40 and spaced from the operative surfaces or edges 44, 46.

In FIG. 4, blade or probe body 12" has a microporous structure (28 in FIG. 5), preferably throughout but at least in the areas between the ends 48 of branch sections 42 and blade edges 44 and 46, enabling fluid penetration to the operative surface or edge from the channel 24".

Those portions of blade or probe body 12, 12', 12" having a microporous structure may be made of sintered material. Blade or probe bodies 12, 12', 12" may be made in their entireties of sintered material.

Probe bodies 12, 12', 12" may be bone cutting blades having a flattened or planar geometry with a pair of opposed major surfaces 50 and 52 (FIG. 1) defined in part by opposed longitudinal edges (e.g., edges 34, 36, 44, 46) and a distal edge (14, FIGS. 1 and 2) of the blade. Blade or probe bodies 12, 12', 12" have an operative surface or edge extending in part along one or both of the longitudinal edges (34, 36; 44, 46) and in part along the distal edge 14. As discussed above, blade or probe bodies 12, 12', 12" are made partially or wholly of sintered material to enable liquid conduction from the infeed channel 24, 24', 24" to the outer surfaces and/or edges of the blade.

Figure 5:
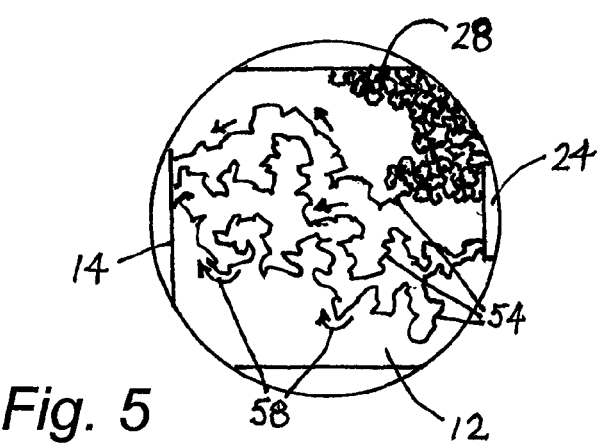
FIG. 5 is an enlarged view of a distal end portion of the ultrasonic surgical tool, blade or probe of FIGS. 1 and 2, corresponding to the area marked V in FIG. 1.

As depicted in FIG. 5, the microporous structure 28 in an ultrasonic tool or probe 10 defines or enables a multiplicity of micropore pathways 54 extending from the liquid infeed channel 24, 24', 24" to the operative surface or edge 14, 34, 36, 44, 46, the probe body having only micropore pathways for liquid flow from channel 24, 24', 24" to the operative surface or edge 14, 34, 36, 44, 46.

In using an ultrasonic microporous surgical tool 10 in a surgical method, one connects shank 16 via connector 18 to source 20 of ultrasonic mechanical vibrations, operatively couples liquid infeed channel 24, 24', 24" to a source 56 (FIG. 1) of liquid, and moves the blade or probe body 12, 12', 12" to a surgical site OT in a patient. One then places an operative surface or edge 14, 34, 36, 44, 46 of the blade or probe body 12, 12', 12" in contact with the organic tissues OT at the surgical site. While the operative surface or edge 14, 34, 36, 44, 46 is in contact with the organic tissues OT, vibration source or transducer 20 is operated to generate ultrasonic mechanical vibrations (generally a standing wave of a predetermined wavelength or frequency) in the blade or probe body 12, 12', 12", thereby ultrasonically vibrating the operative surface or edge 14, 34, 36, 44, 46 at the predetermined frequency. While the operative surface or edge 14, 34, 36, 44, 46 is in contact with the organic tissues OT and during the generating of the ultrasonic mechanical vibrations in the blade or probe body 12, 12', 12", one feeds liquid under pressure from the source 56 of liquid into the liquid infeed channel 24, 24', 24" and from the channel through multiple micropore pathways 54 in the blade or probe body 12, 12', 12" to the operative surface or edge 14, 34, 36, 44, 46, as indicated by arrows 58 in FIG. 5.

Where the blade or probe body is a flattened or planar cutting blade, the method may entail cutting into the organic tissues OT by virtue of the generating of ultrasonic mechanical vibrations in the blade or probe body 12, 12', 12" and the ultrasonic vibrating of the operative surface or edge 14, 34, 36, 44, 46.

Although the invention has been described in terms of particular embodiments and applications, one of ordinary skill in the art, in light of this teaching, can generate additional embodiments and modifications without departing from the spirit of or exceeding the scope of the claimed invention. For instance, while the present invention find particular application in bone cutting blades, it pertains to virtually any ultrasonic instrument where a cooling liquid or a debris-entrainment liquid must be conveyed through the body of the tool to a surface thereof in contact with organic tissues or other target material. Accordingly, it is to be understood that the drawings and descriptions herein are proffered by way of example to facilitate comprehension of the invention and should not be construed to limit the scope thereof.

What is claimed is:

1. An ultrasonic surgical tool comprising a probe body, said probe body having an operative surface or edge contactable with organic tissues for performing a surgical operation on the tissues; and a shank connected to a proximal end of said probe body, said shank being provided at a proximal end, opposite said probe body, with a connector for operatively attaching the tool to a source of ultrasonic mechanical vibrational energy, said shank and a portion of said probe body being formed with a channel for fluid delivery to said probe body, at least a portion of said probe body extending between said channel and said operative surface or edge having a multiplicity of micropore or microchannel pathways extending from said channel to said operative surface or edge and enabling fluid penetration to said operative surface or edge from said channel, said probe body being devoid of other pathways for liquid flow from said channel to said operative surface or edge.

2. The surgical tool defined in claim 1 wherein said channel includes a main section extending longitudinally along said probe body, said channel further including at least one branch section extending at least partially transversely from said main section toward said operative surface or edge, said at least one branch section extending only partway from said main section toward said operative surface or edge, said at least one branch section having a free end opposite said main section and spaced from said operative surface or edge.

3. The surgical tool defined in claim 2 wherein said portion of said probe body is made of sintered material.

4. The surgical tool defined in claim 3 wherein said probe body is made in its entirety of said sintered material.

5. The surgical tool defined in claim 2 wherein said channel includes a plurality of branch sections each extending at least partially transversely from said main section toward said operative surface or edge, each of said branch sections extending only partway from said main section toward said operative surface or edge, each of said branch sections having a respective free end opposite said main section and spaced from said operative surface or edge.

6. The surgical tool defined in claim 1 wherein said portion of said probe body is made of sintered material.

7. The surgical tool defined in claim 6 wherein said probe body is made in its entirety of said sintered material.

8. The surgical tool defined in claim 2 wherein said probe body is a flattened or planar cutting blade having a pair of opposed major surfaces defined by a pair of opposed longitudinal edges and a distal edge of said blade, said operative surface or edge extending in part along one of said longitudinal edges and in part along said distal edge.

9. The surgical tool defined in claim 8 wherein said blade is made of sintered material.

* * * * *